United States Patent [19]

Erpenbach et al.

[11] 4,280,010
[45] Jul. 21, 1981

[54] CONTINUOUS PRODUCTION OF ALKYL ACRYLATES FREE FROM ETHER

[75] Inventors: Heinz Erpenbach, Sürth bei Köln; Klaus Gehrmann, Erftstadt Lechenich; Hans-Klaus Kübbeler, Swisttal; Winfried Lork, Erftstadt Friesheim, all of Fed. Rep. of Germany

[73] Assignee: Hoechst Aktiengesellschaft, Fed. Rep. of Germany

[21] Appl. No.: 66,511

[22] Filed: Aug. 14, 1979

Related U.S. Application Data

[63] Continuation of Ser. No. 744,172, Nov. 22, 1976, abandoned.

[30] Foreign Application Priority Data

Nov. 26, 1975 [DE] Fed. Rep. of Germany ....... 2552987

[51] Int. Cl.$^2$ ............................................. C07C 69/54
[52] U.S. Cl. .................................................... 560/205
[58] Field of Search ........................................ 560/205

[56] References Cited

FOREIGN PATENT DOCUMENTS

| | | |
|---|---|---|
| 1468932 | 12/1968 | Fed. Rep. of Germany ........... 560/205 |
| 2226829 | 12/1973 | Fed. Rep. of Germany ........... 560/205 |
| 2252334 | 5/1974 | Fed. Rep. of Germany ........... 560/205 |

Primary Examiner—Paul J. Killos
Attorney, Agent, or Firm—Connolly and Hutz

[57] ABSTRACT

Alkyl acrylates free from ether are made continuously by reacting acrylic acid with a $C_1$–$C_4$-alkanol, in a molar ratio of 1:1 to 1:2, in liquid phase, at 80° to 130° C., under 100 to 760 mm Hg, in the presence of an acid catalyst.

11 Claims, 1 Drawing Figure

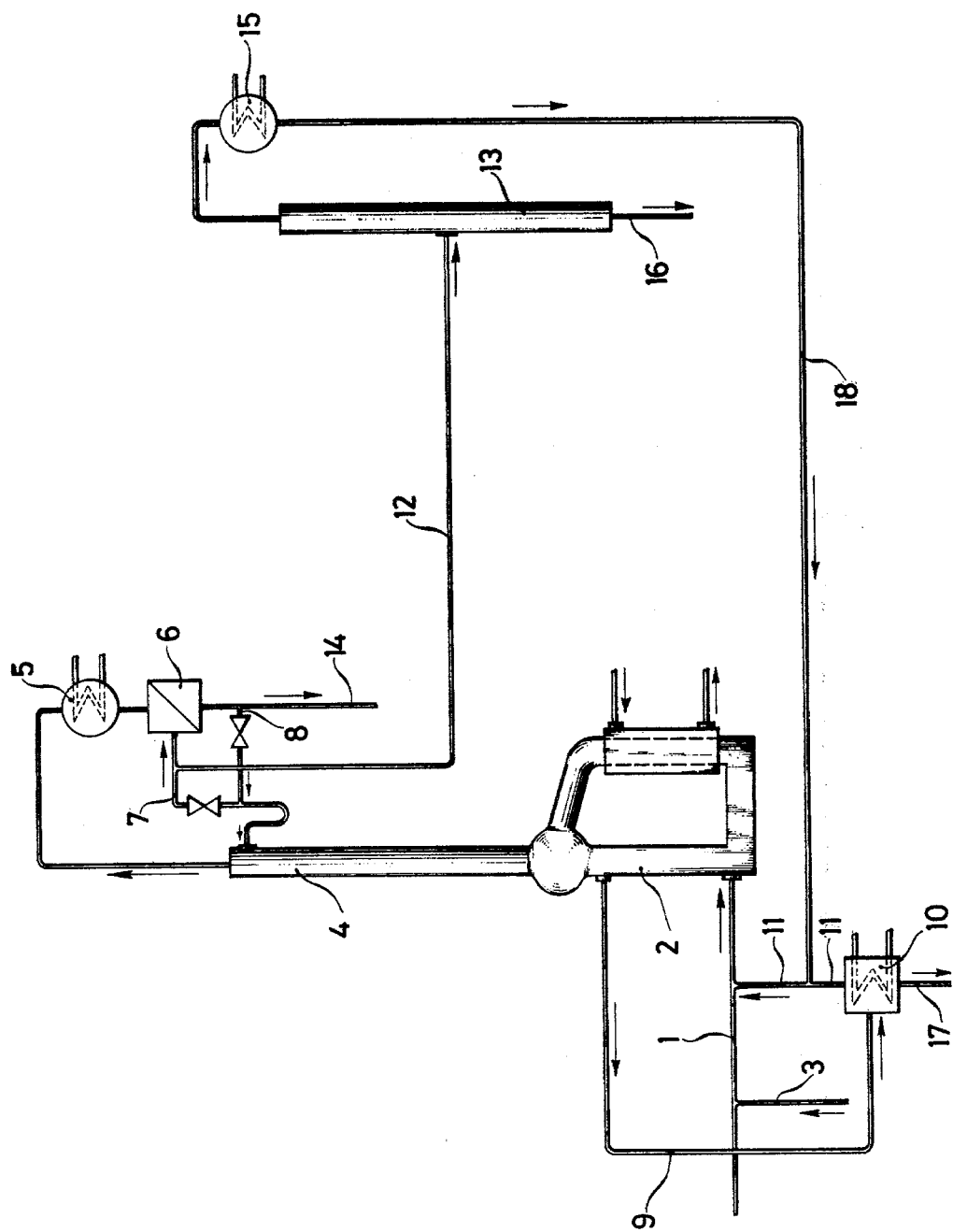

CONTINUOUS PRODUCTION OF ALKYL ACRYLATES FREE FROM ETHER

This application is a continuation of application Ser. No. 744,172 filed Nov. 22, 1976 now abandoned.

Various processes for making alkyl acrylates, wherein acrylic acid is reacted with a $C_1$–$C_4$-alkanol in liquid phase, at elevated temperature and in the presence of a proton-yielding catalyst, have already been described, e.g. in German Patent Specifications "Offenlegungsschriften" Nos. 1,468,932, 2,226,829 and 2,252,334. The processes described therein are concerned with equilibrium reactions, wherein the conversion rate of acrylic acid and alcohol to the ester is critically determined by the equilibrium constant. As a result, it is necessary for unreacted starting material to be separated from the ester produced and to be recycled to the reaction zone, whereby reduction to practice of the process is rendered difficult.

In an attempt to increase the acrylic acid conversion rate to the respective ester, it has been proposed to use the alcohol in a proportion up to five times the molar proportion of acrylic acid, to remove the reaction water by azeotropic distillation, or to extract the ester by means of a solvent during the reaction. It has also been suggested that these steps be coupled with the use of high catalyst concentrations. This, however, is not satisfactory in respect of the following points: It is necessary for a large excess of alcohol to be recovered, or for the distillation aid or extractant to be separated. In addition to this, a considerable quantity of undesirable ether by-product, corresponding to the alcohol used in each particular case, is obtained. A still further problem encountered with these prior processes resides in the high catalyst concentration in the esterification residue which is very difficult to dispose of under ecologically beneficial conditions.

This problem is more particularly encountered in the production of acrylic acid esters of $C_1$ and $C_2$-alkanols, where it is necessary to use the catalyst in high concentrations, e.g. 5 to 50 weight % of $H_2SO_4$ or 10 to 80 weight % of organic sulfonic acid, which give rise to increased formation of ether.

In reacting acrylic acid with a $C_4$-alkanol, it is quite customary for the resulting reaction water to be removed azeotropically by means of an excess of alcohol. Despite the displacement of equilibrium which is associated therewith, it is not possible in this manner to achieve complete conversion of the acrylic acid. In view of the fact that n-butyl acrylate and acrylic acid substantially have identical boiling points, it is necessary in an attempt to purify n-butyl acrylate to first neutralize the acrylic acid and to then extract the resulting salt by means of water. This, however, is a rather expensive operation producing pollutive waste water.

The present invention now provides a continuous process for making alkyl acrylates free from ether by reacting acrylic acid with a $C_1$–$C_4$-alkanol, in a molar ratio of 1:1 to 1:2, in liquid phase, at temperatures of 80 to 130° C., under pressures of 100 to 760 mm Hg, in the presence of an acid catalyst, and distillatively purifying the resulting ester, which comprises: continuously introducing a reaction mixture of acrylic acid, alkanol and a sulfuric acid or organic sulfonic acid catalyst into a reaction zone, the reaction mixture containing sulfuric acid in a concentration of 0.1 to 3 weight %, or the organic sulfonic acid in a concentration of 1 to 8 weight %; reacting the reaction mixture over a period of 4 to 10 hours in the reaction zone, distilling off, near the head of a first distilling zone mounted on the reaction zone, an azeotropic mixture of alkyl acrylate, reaction water and unreacted alkanol; condensing the mixture, and separating the mixture into an aqueous phase and organic phase; recycling a portion of the organic phase and, in the event of the alkanol used being a $C_3$ or $C_4$-alkanol, also a portion of the aqueous phase to the head of the first distilling column, and removing the remaining aqueous phase; delivering the balance portion of the organic phase to a second distilling zone, distilling off overhead an azeotropic mixture of alkanol and ester, condensing the mixture, recycling it to the reaction zone, and removing ether-free alkyl acrylate through the base portion of the second distilling zone; continuously taking a portion of reaction mixture from the reaction zone, distillatively freeing said reaction mixture from high-boiling matter, admixing the resulting distillate with a quantity of catalyst equivalent to that removed together with said high-boiling matter, and then recycling the distillate to the reaction zone.

Further preferred features of the present process provide:

(a) for a concentration of 0.5 to 2 weight % of sulfuric acid to be maintained in the reaction zone;

(b) for a concentration of 1.5 to 5 weight % of sulfonic acid to be maintained in the reaction zone;

(c) for the alkanol to be selected from methanol, ethanol, n-propanol, iso-propanol, n-butanol, isobutanol, secondary butanol or tertiary butanol;

(d) for the organic sulfonic acid to be selected from benzenesulfonic acid and toluenesulfonic acid;

(e) for a 20 to 90 weight % proportion of the organic phase to be recycled to the head of the first distilling zone;

(f) in the event of the alkanol used being a $C_3$ or $C_4$-alkanol for a 50 to 100 weight % proportion of the aqueous phase to be recycled to the head of the first distilling zone;

(g) in the event of the alkanol used being a $C_3$ or $C_4$-alkanol for the balance portion of the organic phase to be dehydrated in conventional manner and to be then delivered to the second distilling zone;

(h) for the organic phase to be distilled in the second distilling zone under pressure of 100 to 760 mm Hg; and (i) for a 0.1 and 2 weight % proportion of the reaction mixture to be taken from the reaction zone and to be distillatively freed in an evaporation zone at temperatures of 120° to 180° C., under pressures of 80 to 650 mm Hg from high-boiling matter.

The esterification may preferably be effected at temperatures of 85° to 110° C. Temperatures higher than specified favor the formation of ether and polymerization, whereas temperatures lower than specified herein considerably affect the reaction velocity.

The esterification reaction and distillative separation are preferably effected in the presence of 0.01 to 0.1 weight % of a suitable polymerization inhibitor, which may be selected, for example, from hydroquinone, hydroquinone monomethylether, p-benzoquinone, phenothiazine or methylene blue, and may be used in combination with air, if desired or convenient.

The $C_1$–$C_4$-alkanol starting materials may be used in admixture with some minor proportion of water or final ester. With respect to the acrylic acid and respective alcohol, it is necessary for them to be introduced into the reaction zone in a molar ratio of 1:1.1 to 1:1.5. The use of a molar ratio smaller than specified herein has been found to adversely affect the reaction velocity and conversion rate, whereas the use of a molar ratio greater than specified herein has been found to favor the formation of an undesirable ether by-product.

A preferred version of the present process will now be described more fully with reference to the accompanying flow scheme.

A reactor (2) is supplied through a conduit (1) with acrylic acid and $C_1$-$C_4$-alkanol, which are kept circulating therein by the thermo-principle. Through a conduit (3), the reactor (2) is supplied with the quantity of sulfuric acid necessary for the reaction mixture under circulation to contain approximately 1 to 2 weight % of sulfuric acid. Near the head of a column (4) mounted on the reactor (2), there is distilled off an azeotropic mixture of ester, excess alcohol and water, at a temperature of 95°–96° C. and under a pressure of 100 to 760 mm Hg in the reactor (2). After condensation in a condenser (5) and phase separation in a separator (6), a portion of the organic phase is recycled through a conduit (7) to the column (4) for distillative removal of water, the acrylic acid being retained therein. In those cases in which the alkanol used is a $C_3$ or $C_4$ alkanol (a propanol or butanol), the column (4) is also supplied through a conduit (8) with a portion of the aqueous phase for distillative separation of the ester.

The volume of material under circulation is kept constant. To this end, a portion of the reaction medium is taken through a conduit (9), freed in an evaporator (10) at 120° to 180° C. and under 80 to 650 mm Hg from high-boiling matter, and recycled to the reactor (2) through a conduit (11). The quantity of sulfuric acid removed together with base product through a conduit (17) is replaced by supplying an equivalent quantity of acid through the conduit (3).

The balance of the organic phase is delivered from the separator (6) through a conduit (12) to a further distilling column (13), and residual reaction water is removed through a conduit (14). Near the head of the distilling column (13), which is operated under a pressure of 100 to 760 mm Hg, there is obtained an azeotropic mixture of alcohol and ester. The mixture is condensed in a cooler (15) and recycled to the reactor (2) through a conduit (18) and the conduit (11). Crude ester is obtained in the base of the column (13) from which it is taken through a conduit (16) and distilled until pure.

EXAMPLE 1:

The reactor (2) was a stainless steel/glass circulation reactor. The capacity was 18 l of reaction mixture containing 1 weight % of a sulfuric acid catalyst, under the operational conditions selected. One side of the reactor was jacketed and heated by means of steam. The reaction temperature was 95° C. and the pressure 760 mm Hg. The reactor (2) was fed with 1404 g/h (19.5 mol) of fresh acrylic acid and 634 g/h (19.8 mol) of fresh methanol (through the conduit 1). Partially unreacted material was recycled through the conduits (11) and (18). In other words, the reactor (2) was fed with altogether 2561 g/h (density=0.95 g/cm$^3$) of a mixture composed of 1451 g/h (20.15 mol) of acrylic acid, 839 g/h (26.2 mol) of methanol and 271 g/h (3.15 mol) of methyl acrylate. Acrylic acid and methanol were accordingly used in a molar ratio of 1:1.3. After a residence time of 6.7 hours in the reactor, 97% of the acrylic acid used was found to have been transformed. 8920 g/h of material was distilled off at 69° C. at atmospheric pressure near the head of the distilling column (4) mounted on the reactor, and separated into two phases in the separator (6). 6.8 l/h (=6450 g/h) of organic phase was recycled to the column (4) through the recycle line (7) and used as an entrainer for reaction water. 240 g/h of aqueous phase was removed through the conduit (14). The remaining 2230 g/h of organic phase was taken from the separator (6) and delivered through the conduit (12) to the second distilling column (13), which was operated under a pressure of 760 mm Hg, at a head temperature of 61° C., at a base temperature of 71° C., and at a reflux ratio of 6, and in which altogether 470 g/h of an azeotrope consisting of 205 g/h of methanol and 265 g/h of methyl acrylate was distilled off and recycled to the reactor (2) through the conduits (18) and (11). The recycle material was free from dimethylether. Crude methyl acrylate was retained in the base of the column (13). After dehydration and distillation until pure, which gave a further 110 g/h of reaction water (altogether 350 g/h of reaction water), pure methyl acrylate was obtained at a rate of 1625 g/h (18.9 mol). The yield was 96.9%, based on the acrylic acid which underwent conversion. The methyl acrylate so made had a purity of 99.8% and it was free from dimethylether.

The quantity of reaction medium circulated in the reactor (2) was kept constant. To this end, 101 g per hour of reaction mixture containing 1 weight % of sulfuric acid was taken from the reactor (2) through the conduit (9). High boiling matter (48 g) was separated in the evaporator (10) at 130° to 160° C. under 350 mm Hg and removed through the conduit (17). Next, 53 g/h of distillate (47 g/h of acrylic acid +6 g/h of methyl acrylate) was recycled to the reactor (2) through the conduit (11). The quantity of $H_2SO_4$ removed together with base product was replaced by the supply (through the conduit 3) of an equivalent quantity of sulfuric acid to the reaction medium under circulation in the reactor (2).

EXAMPLE 2

The procedure was the same as that described in Example 1, but the sulfuric acid catalyst in the reaction medium under circulation in the reactor (2) was replaced by 2.5 weight % of a para-toluenesulfonic acid catalyst. The reaction temperature was 95° C. and the pressure 760 mm Hg. The reactor (2) was fed with 1119 g/h (15.5 mol) of fresh acrylic acid and 499 g/h (15.6 mol) of fresh methanol (through the conduit 1). Partially unreacted material was recycled through the conduits (11) and (18). In other words, the reactor (2) was fed with altogether 1969 g/h of a mixture composed of 1171 g/h (16.3 mol) of acrylic acid, 676 g/h (21.1 mol) of methanol and 122 g/h (1.4 mol) of methyl acrylate. Acrylic acid and methanol were accordingly used in a molar ratio of 1:1.3. After a residence time of 8.6 hours in the reactor, 95.7% of the acrylic acid used was found to have been transformed. 6814 g/h of material was distilled off at 69° C. at atmospheric pressure near the head of the distilling column (4) mounted on the reactor, and separated into two phases in the separator (6). 5.2 l/h (=4962 g/h) of organic phase was recycled to the column (4) through the recycle line (7) and used as an entrainer for reaction water. 198 g/h of aqueous phase was removed through the conduit (14). The remaining 1654 g/h of organic phase was taken from the separator (6) and delivered through the conduit (12) to the second distilling column (13), which was operated under a pressure of 760 mm Hg, at a head temperature of 61° C., at a base temperature of 71° C., and at a reflux ratio of 6, and in which altogether 298 g/h of an azeotrope consisting of 177 g/h of methanol and 121 g/h of methyl acrylate was distilled off and recycled to the reactor (2) through the conduits (18) and (11). The recycle material was free from dimethylether. Crude methyl acrylate was retained in the base of the column (13). After dehydration and distillation until pure, which gave a further 64 g/h of reaction water (altogether 262 g/h of reaction water), pure methyl acrylate was obtained at a rate of 1290 g/h (15 mol), which had a purity of 99.95% and was free from dimethylether. The yield was 96.8%, based on the acrylic acid which underwent conversion.

The quantity of reaction medium circulated in the reactor (2) was kept constant. To this end, 115 g/h of reaction mixture containing 2.5 weight % of p-toluenesulfonic acid was taken from the reactor (2) through the conduit (9). High boiling matter (62 g/h) was separated in the evaporator (10) at 130 to 160° C. under 350 mm Hg and removed through the conduit (17). Next, 53 g/h of distillate (52 g/h of acrylic acid +1 g/h of methyl acrylate) was recycled to the reactor (2) through the conduit (11). The quantity of p-toluenesulfonic acid removed together with base product was replaced by the supply (through the conduit 3) of an equivalent quantity of acid to the reaction medium under circulation in the reactor (2).

EXAMPLE 3

The reactor (2) was a stainless steel/glass circulation reactor. The capacity was 21 l of reaction mixture containing 2 weight % of a sulfuric acid catalyst, under the operational conditions selected. One side of the reactor was jacketed and heated by means of steam. The reaction temperature was 96° C. and the pressure 300 mm Hg. The reactor (2) was fed with 1044 g/h (14.5 mol) of fresh acrylic acid and 1162 g/h (15.7 mol) of fresh n-butanol (through the conduit 1). Partially unreacted material was recycled through the conduits (11) and (18). In other words, the reactor (2) was fed with altogether 3049 g/h (density=0.89 g/cm$^3$) of a mixture composed of 1145 g/h (15.9 mol) of acrylic acid, 1766 g/h (23.9 mol) of n-butanol and 138 g/h (1.08 mol) of n-butyl acrylate. Acrylic acid and butanol were accordingly used in a molar ratio of 1:1.5. After a residence time of 6.13 hours in the reactor, 91.2 of the acrylic acid used was found to have been transformed. 5620 g/h of material was distilled off at 77° C. under a pressure of 300 mm Hg near the head of the distilling column (4) mounted on the reactor, and separated into two phases in the separator (6). 1.2 l/h (=1044 g/h) of organic phase was recycled to the column (4) through the recycle line (7) to retain acrylic acid therein, and 1800 g/h of aqueous phase was recycled through the conduit (8) and used as an entrainer for the n-butyl acrylate produced. 129 g/h of aqueous phase was removed through the conduit (14). The remaining 2647 g/h of organic phase was taken from the separator (6) and delivered through the conduit (12) to a dehydration stage (not shown in the drawing) in which a further 132 g/h of reaction water (altogether 261 g/h of reaction water) was obtained. In the column (13), which was operated under a pressure of 400 mm Hg, at a head temperature of 93° C., at a base temperature of 131° C., and at a reflux ratio of 1.5, the butanol in excess (600 g) and 105 g of n-butyl acrylate were distilled off and recycled to the reactor (2) through the conduits (18) and (11). Crude n-butyl acrylate was obtained in the base of the column (13). After distillation until pure, n-butyl acrylate of 99.9% strength was obtained at a rate of 1792 g/h (14 mol), which was free from dibutylether. The yield was 96.6%, based on the acrylic acid which underwent conversion.

The quantity of reaction medium circulated in the reactor (2) was kept constant. To this end, 273 g/h of reaction mixture containing 2 weight % of sulfuric acid was taken from the reactor (2) through the conduit (9). High boiling matter (135 g) was separated in the evaporator (10) at 125° to 165° C. under 100 mm Hg and removed through the conduit (17). Next, 138 g/h of distillate (101 g/h of acrylic acid+33 g/h of n-butyl acrylate+4 g/h of n-butanol) was recycled to the reactor (2) through the conduit (11). The quantity of H$_2$SO$_4$ removed together with base product was replaced by the supply (through the conduit 3) of an equivalent quantity of sulfuric acid to the reaction medium under circulation in the reactor (2).

The reaction mixtures, distillates and reflux materials used in the above Examples were all stabilized with 0.05 weight % of a phenothiazine/p-benzoquinone mixture.

We claim:

1. An improved process for the continuous production of alkyl acrylates free from ether by reacting acrylic acid with a C$_1$–C$_4$-alkanol, in a molar ratio of 1:1 to 1:2, in liquid phase, at temperatures of 80° to 130° C., under pressures of 100 to 760 mm Hg, in the presence of an acid catalyst, the improvement which is: continuously introducing essentially only a reaction mixture of acrylic acid, alkanol and a sulfuric acid or organic sulfonic acid catalyst into a reaction zone, the reaction mixture containing sulfuric acid in a concentration of 0.1 to 3 weight %, or the organic sulfonic acid in a concentration of 1 to 8 weight %, reacting the reaction mixture over a period of 4 to 10 hours in the reaction zone, distilling off, near the head of a first distilling zone mounted on the reaction zone, an azeotropic mixture of alkyl acrylate, reaction water and unreacted alkanol; condensing the mixture, and separating the mixture into an aqueous phase and organic phase; recycling a portion of the organic phase to the head of the first distilling column, and removing the remaining aqueous phase; delivering the balance portion of the organic phase to a second distilling zone, distilling off overhead an azeotropic mixture of alkanol and ester, condensing the mixture, recycling it to the reaction zone, and removing ether-free alkyl acrylate through the base portion of the second distilling zone; continuously taking a portion of reaction mixture from the reaction zone, distillatively freeing said reaction mixture from high-boiling matter, admixing the resulting distillate with a quantity of catalyst equivalent to that removed together with said high-boiling matter, and then recycling the distillate to the reaction zone.

2. Process as claimed in claim 1, wherein a concentration of 0.5 to 2 weight % of sulfuric acid is maintained in the reaction zone.

3. Process as claimed in claim 1, wherein a concentration of 1.5 to 5 weight % of organic sulfonic acid is maintained in the reaction zone.

4. Process as claimed in claim 1, wherein the alkanol used is a member selected from the group consisting of methanol, ethanol, n-propanol, iso-propanol, n-butanol, iso-butanol, secondary butanol or tertiary butanol.

5. Process as claimed in claim 1, wherein the organic sulfonic acid is a member selected from the group consisting of benzenesulfonic acid and toluenesulfonic acid.

6. Process as claimed in claim 1, wherein a 20 to 90 weight % proportion of the organic phase is recycled to the head of the first distilling zone.

7. Process as claimed in claim 1, wherein, in the event of the alkanol used being a $C_3$ or $C_4$-alkanol, a portion of the organic phase and also a portion of the aqueous phase are recycled to the head of the first distilling zone.

8. Process as claimed in claim 1, wherein, in the event of the alkanol used being a $C_3$ or $C_4$-alkanol, a portion of the organic phase and also a 50 to 100 weight % proportion of the aqueous phase are recycled to the head of the first distilling zone.

9. Process as claimed in claim 1, wherein, in the event of the alkanol used being a $C_3$ or $C_4$-alkanol, the balance portion of the organic phase is dehydrated and then delivered to the second distilling zone.

10. Process as claimed in claim 1, wherein the organic phase is distilled in the second distilling zone under pressures of 100 to 760 mm Hg.

11. Process as claimed in claim 1, wherein a 0.1 to 2 weight % proportion of the reaction mixture is taken from the reaction zone and distillatively freed in an evaporation zone at temperatures of 120° to 180° C., under pressures of 80 to 650 mm Hg from high-boiling matter.

* * * * *